US010921323B2

(12) United States Patent
Soutschek et al.

(10) Patent No.: US 10,921,323 B2
(45) Date of Patent: Feb. 16, 2021

(54) METHOD FOR THE IMMUNOLOGICAL DIAGNOSIS OF A SAMPLE WITH A POTENTIAL INFECTION WITH AN ARBOVIRUS AND TEST KITS SUITABLE FOR THIS PURPOSE

(71) Applicant: Mikrogen GmbH, Neuried (DE)

(72) Inventors: Erwin Soutschek, Berg (DE); Oliver Boecher, Neuried (DE); Christina Noelting, Munich (DE)

(73) Assignee: Mikrogen GmbH, Neuried (DE)

( * ) Notice: Subject to any disclaimer, the term of this patent is extended or adjusted under 35 U.S.C. 154(b) by 95 days.

(21) Appl. No.: 16/336,026

(22) PCT Filed: Oct. 17, 2017

(86) PCT No.: PCT/EP2017/076411
§ 371 (c)(1),
(2) Date: Mar. 22, 2019

(87) PCT Pub. No.: WO2018/073208
PCT Pub. Date: Apr. 26, 2018

(65) Prior Publication Data
US 2019/0227065 A1    Jul. 25, 2019

(30) Foreign Application Priority Data
Oct. 19, 2016    (EP) .................................... 16194496

(51) Int. Cl.
*G01N 33/53*    (2006.01)
*A61K 39/12*    (2006.01)
*A61K 39/295*    (2006.01)
*G01N 33/569*    (2006.01)

(52) U.S. Cl.
CPC ....... *G01N 33/56983* (2013.01); *A61K 39/12* (2013.01); *A61K 39/295* (2013.01); *G01N 33/53* (2013.01); *G01N 2333/185* (2013.01); *Y02A 50/30* (2018.01)

(58) Field of Classification Search
None
See application file for complete search history.

(56) References Cited

U.S. PATENT DOCUMENTS

2004/0197769 A1   10/2004   Wong et al.

FOREIGN PATENT DOCUMENTS

WO    WO 2016/022071 A1    2/2016
WO    WO 2016/069245 A1    5/2016

OTHER PUBLICATIONS

Gyurech et al., False positive dengue NS1 antigen test in a traveller with an acute Zika virus infection imported into Switzerland, 2016, Swiss Medical Weekly, 146.*

PCT/EP2017/076411—International Search Report, dated Feb. 5, 2018.
PCT/EP2017/076411—International Written Opinion, dated Feb. 5, 2018.
PCT/EP2017/076411—International Preliminary Report on Patentability, dated Mar. 18, 2019.
Ginier, et al., "Zika without symptoms in returning travelers: What are the implications?", Travel Medicine and Infectious Disease, Elsevier, Amsterdam Netherlands, vol. 14, No. 1, pp. 16-20, Feb. 5, 2016.
Francisco J. Carod-Artal, "Epidemiology and neurological complications of infection by the Zika virus: a new emerging nerotropic virus", Revista de Neurologia, Viguera Editores, Spain, vol. 62, No. 7, pp. 317-328, Apr. 1, 2016.
Shu, et al., "Current status of dengue diagnosis at the Center for Disease Control, Taiwan", Dengue Bulletin, vol. 28, pp. 107-117, Jan. 1, 2004.
Yen, et al., "Multicolored silver nanoparticles for multiplexed disease diagnostics: distingushing dengue, yellow fever, and Ebola viruses", Lab on a Chip, vol. 15, No. 7, pp. 1638-1641, Jan. 1, 2015.
Basile, et al., "Multiplex microsphere immunoassys for the detection of IgM and IgG to arboviral diseases", PLOS ONE, vol. 8, No. 9, p. e75670, Sep. 25, 2013.
Anonymous: "Zika/Dengue/Chikungunya Combos", Jul. 2, 2016, XP055359891.

(Continued)

*Primary Examiner* — Benjamin P Blumel
(74) *Attorney, Agent, or Firm* — Curatolo Sidoti Co., LPA; Salvatore A Sidoti; Floyd Trillis, III (57) ABSTRACT

The present invention relates to a method for the immunological diagnosis of a sample from a patient with a potential infection with an arbovirus, wherein
a) a sample is brought into contact with a plurality of antigens that, separated from each other, are applied to a solid phase, wherein at least the following antigens are used:
  aa) the "non-structural protein 1" of a first arbovirus or an immunologically reactive part thereof having at least 8 amino acids,
  bb) an "envelope protein" of a first arbovirus or an immunologically reactive part thereof having at least 8 amino acids,
  cc) an "envelope protein" of a second arbovirus or an immunologically reactive part thereof having at least 8 amino acids,
  dd) the "non-structural protein 1" of a third arbovirus or an immunologically reactive part thereof having at least 8 amino acids and
  ee) an "envelope protein" of a third arbovirus or an immunologically reactive part thereof having at least 8 amino acids,
b) the solid phase is washed to separate non-specific bindings,
c) the immune complex formed on the solid phase is converted into a signal and
d) the test method is evaluated by comparing the relative signal strengths.

10 Claims, 5 Drawing Sheets

Specification includes a Sequence Listing.

(56) References Cited

OTHER PUBLICATIONS

Anonymous: "Zika virus envelop (Env) and NS1 protein ELISA kits", Jul. 14, 2016, XP055359652.
Anonymous: "Zika virus infections", Jul. 1, 2016, XP055359072.

* cited by examiner

Figure 1:
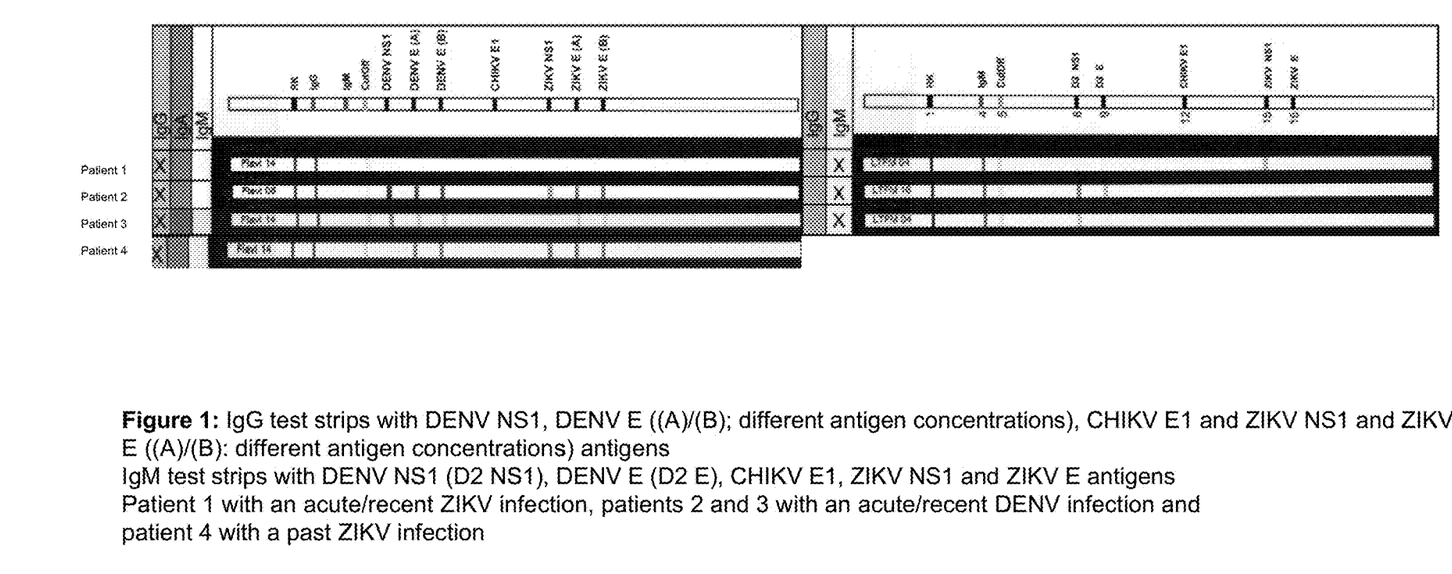
FIG. 1 shows IgG test strips with DENV NS1, DENV E ((A)/(B); different antigen concentrations), CHIKV E1 and ZIKV NS1 and ZIKV E ((A)/(B): different antigen concentrations) antigens, and IgM test strips with DENV NS1 (D2 NS1), DENV E (D2 E), CHIKV E1, ZIKV NS1 and ZIKV E antigens. Patient 1 with an acute/recent ZIKV infection, patients 2 and 3 with an acute/recent DENV infection and patient 4 with a past ZIKV infection.

Figure 1: IgG test strips with DENV NS1, DENV E ((A)/(B); different antigen concentrations), CHIKV E1 and ZIKV E ((A)/(B); different antigen concentrations) antigens
IgM test strips with DENV NS1 (D2 NS1), DENV E (D2 E), CHIKV E1, ZIKV NS1 and ZIKV E antigens
Patient 1 with an acute/recent ZIKV infection, patients 2 and 3 with an acute/recent DENV infection and patient 4 with a past ZIKV infection

Figure 2:
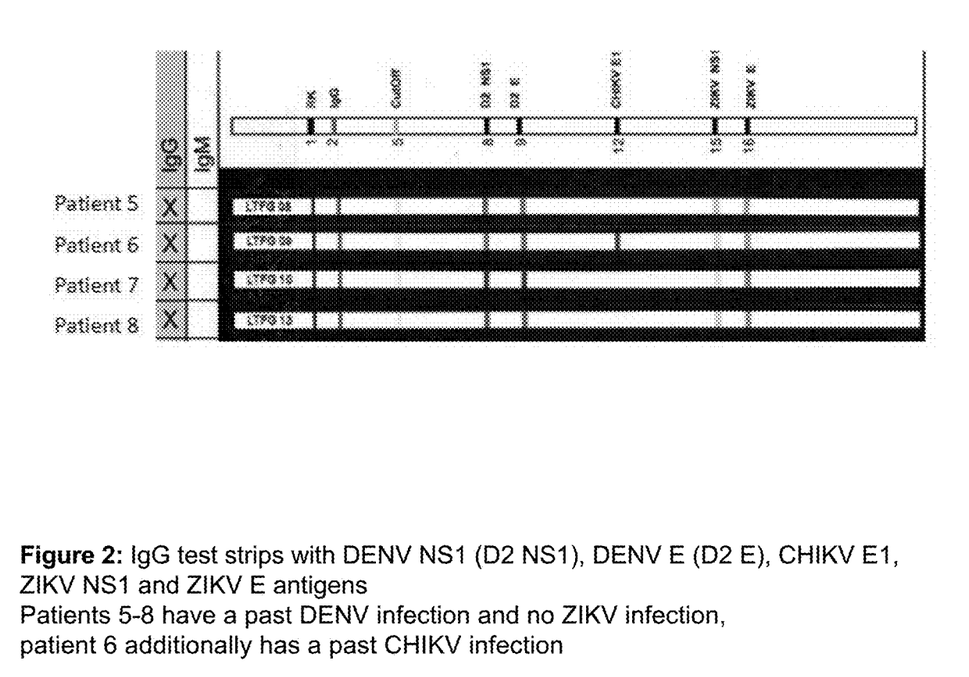
FIG. 2 shows IgG test strips with DENV NS1 (D2 NS1), DENV E (D2 E), CHIKV E1, ZIKV NS1 and ZIKV E antigens. Patients 5-8 have a past DENV infection and no ZIKV infection, patient 6 additionally has a past CHIKV infection.

Figure 2: IgG test strips with DENV NS1 (D2 NS1), DENV E (D2 E), CHIKV E1, ZIKV NS1 and ZIKV E antigens
Patients 5-8 have a past DENV infection and no ZIKV infection, patient 6 additionally has a past CHIKV infection Figure 3: IgG test strips with yellow fever NS1 in two different antigen concentrations (YFV NS1), CHIKV E1 (CHIKV E1) and DENV NS1 (DENV NS1) antigens IgG test strips of patients with yellow fever vaccination (patient 9), patient 10 with yellow fever vaccination and past Chikungunya and DENV infections, patient 11 with singular dengue virus infection, patient 12 is a healthy blood donor without the above-mentioned infections and patient 13 is a patient infected with the West Nile virus.

Figure 4:
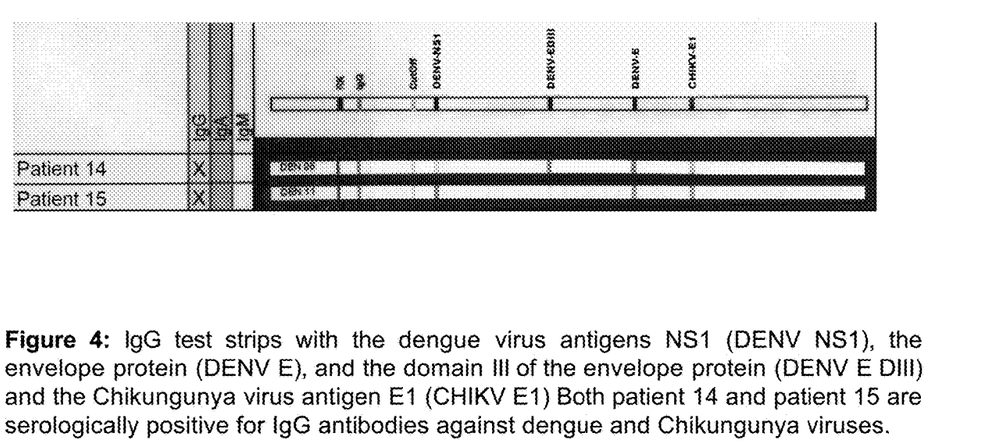
FIG. 4 shows IgG test strips with the dengue virus antigens NS1 (DENV NS1), the envelope protein (DENV E), and the domain III of the envelope protein (DENV E DIII) and the Chikungunya virus antigen E1 (CHIKV E). Both patient 14 and patient 15 are serologically positive for IgG antibodies against dengue and Chikungunya viruses.

Figure 4: IgG test strips with the dengue virus antigens NS1 (DENV NS1), the envelope protein (DENV E), and the domain III of the envelope protein (DENV E DIII) and the Chikungunya virus antigen E1 (CHIKV E1) Both patient 14 and patient 15 are serologically positive for IgG antibodies against dengue and Chikungunya viruses.

Figure 5:
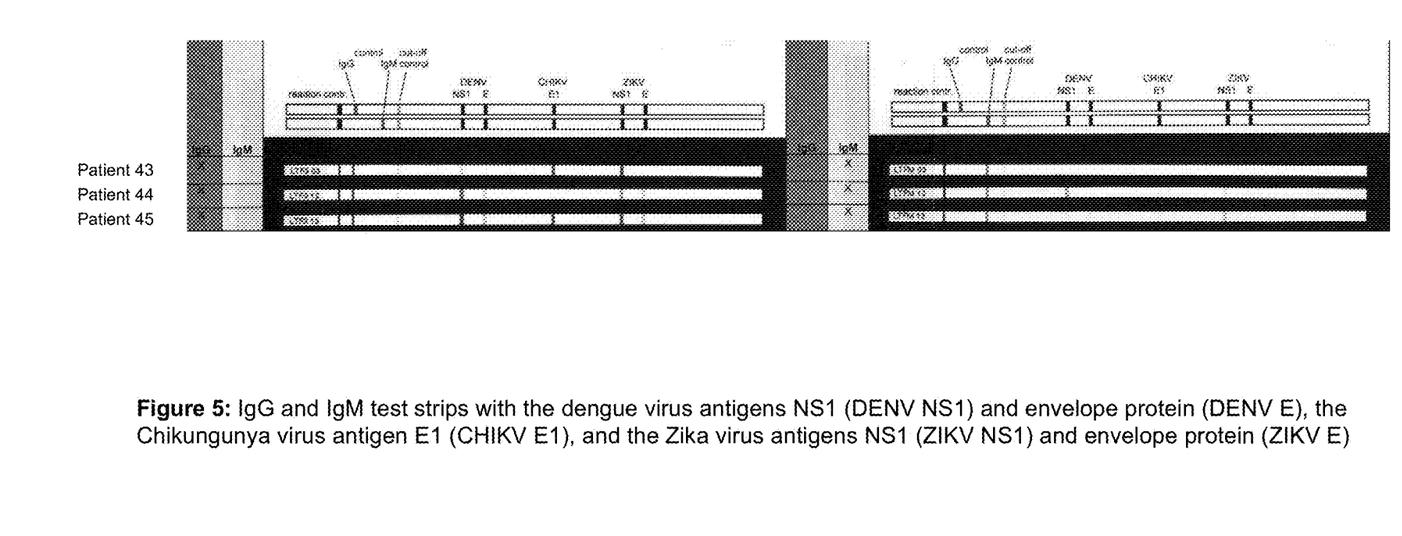
FIG. 5 shows IgG and IgM test strips with the dengue virus antigens NS1 (DENV NS1) and envelope protein (DENV E), the Chikungunya virus antigen E1 (CHIKV E1), and the Zika virus antigens NS1 (ZIKV NS1) and envelope protein (ZIKV E).

Figure 5: IgG and IgM test strips with the dengue virus antigens NS1 (DENV NS1) and envelope protein (DENV E), the Chikungunya virus antigen E1 (CHIKV E1), and the Zika virus antigens NS1 (ZIKV NS1) and envelope protein (ZIKV E)

```
                        SEQUENCE LISTING

<160> NUMBER OF SEQ ID NOS: 5

<210> SEQ ID NO 1
<211> LENGTH: 114
<212> TYPE: PRT
<213> ORGANISM: Dengue virus

<400> SEQUENCE: 1

Met Tyr Ser Met Cys Thr Gly Lys Phe Lys Val Val Lys Glu Ile Ala
1               5                   10                  15

Glu Thr Gln His Gly Thr Ile Val Ile Arg Val Gln Tyr Glu Gly Asp
            20                  25                  30

Gly Ser Pro Cys Lys Ile Pro Phe Glu Ile Met Asp Leu Glu Lys Arg
        35                  40                  45

His Val Leu Gly Arg Leu Ile Thr Val Asn Pro Ile Val Thr Glu Lys
    50                  55                  60

Asp Ser Pro Val Asn Ile Glu Ala Glu Pro Pro Phe Gly Asp Ser Tyr
65                  70                  75                  80

Ile Ile Ile Gly Val Glu Pro Gly Gln Leu Lys Leu Asn Trp Phe Lys
                85                  90                  95

Lys Gly Leu Glu Val Leu Phe Gln Gly Pro His His His His His His
            100                 105                 110

His His

<210> SEQ ID NO 2
<211> LENGTH: 117
<212> TYPE: PRT
```

```
<213> ORGANISM: Zika virus

<400> SEQUENCE: 2

Met Tyr Ser Leu Cys Thr Ala Ala Phe Thr Phe Thr Lys Ile Pro Ala
1               5                   10                  15

Glu Thr Leu His Gly Thr Val Thr Val Glu Val Gln Tyr Ala Gly Thr
            20                  25                  30

Asp Gly Pro Cys Lys Val Pro Ala Gln Met Ala Val Asp Met Gln Thr
        35                  40                  45

Leu Thr Pro Val Gly Arg Leu Ile Thr Ala Asn Pro Val Ile Thr Glu
    50                  55                  60

Ser Thr Glu Asn Ser Lys Met Met Leu Glu Leu Asp Pro Pro Phe Gly
65                  70                  75                  80

Asp Ser Tyr Ile Val Ile Gly Val Gly Glu Lys Lys Ile Thr His His
                85                  90                  95

Trp His Arg Ser Gly Leu Glu Val Leu Phe Gln Gly Pro His His His
            100                 105                 110

His His His His His
        115

<210> SEQ ID NO 3
<211> LENGTH: 32
<212> TYPE: PRT
<213> ORGANISM: Dengue virus

<400> SEQUENCE: 3

Lys Arg Ser Leu Arg Pro Gln Pro Thr Glu Leu Lys Tyr Ser Trp Lys
1               5                   10                  15

Thr Trp Gly Lys Ala Lys Met Leu Ser Thr Glu Ser His Asn Gln Thr
            20                  25                  30

<210> SEQ ID NO 4
<211> LENGTH: 15
<212> TYPE: PRT
<213> ORGANISM: Dengue virus

<400> SEQUENCE: 4

Pro Trp His Leu Gly Lys Leu Glu Met Asp Phe Asp Phe Cys Asp
1               5                   10                  15

<210> SEQ ID NO 5
<211> LENGTH: 24
<212> TYPE: PRT
<213> ORGANISM: Dengue virus

<400> SEQUENCE: 5

Asp Ser Gly Cys Val Val Ser Trp Lys Asn Lys Glu Leu Lys Cys Gly
1               5                   10                  15

Ser Gly Ile Phe Ile Thr Asp Asn
            20
```

METHOD FOR THE IMMUNOLOGICAL DIAGNOSIS OF A SAMPLE WITH A POTENTIAL INFECTION WITH AN ARBOVIRUS AND TEST KITS SUITABLE FOR THIS PURPOSE

CROSS REFERENCE TO RELATED APPLICATIONS

This application is a national stage application under 35 U.S.C. § 371 of International Application No. PCT/EP2017/076411, filed 17 Oct. 2017, which claims priority from European Patent Application No. 16194496.2, filed 19 Oct. 2016, which applications are hereby incorporated herein by reference in their entireties.

The object of the present invention is a method for the immunological diagnosis of a sample from a patient with a potential infection with an arbovirus, and test kits suitable for this purpose.

Viruses that are transmitted by insects (above all midges) or Arachnida (for example, ticks) are referred to as arboviruses (arthropod-borne viruses). Required for the transmission of viruses by arthropods is that the viruses can infect specific organs of the animals (above all mosquitos), such as for example the epithelial cells of the gut or the salivary glands. In principle, the uptake of blood containing viruses by arthropods alone is not sufficient. Rather, the viruses must be able to go through a productive infection cycle both in arthropods and in mammalian cells.

Due to the extremely strong increase in travel and global trade in recent years, both viruses and midges have been brought to areas where they were not originally endemic. Thereby, diseases and local epidemics may also occur in places where they have not been observed before. In addition, the strong industrialization and the associated increasing population density play an essential role in the spread of epidemics.

A large part of the population travels to geographically distant areas and it is therefore often difficult to diagnose with which virus the patient has been infected. Moreover, it is quite probable that infections with several different viruses are present and the patient may have previously experienced a potentially inapparent viral infection. At present, four different serotypes of dengue virus are known. One having had an infection does not have permanent immunoprotection from infections with another serotype of the dengue virus. It is therefore possible that the same patient comes down with dengue several times. A further problem are cross-reactivities that can occur due to the genetic relationship of the viruses and the similarities of the antigens. A further complication of the diagnostics can be caused by vaccinations (for example, against the yellow fever virus).

Cleton et al. (PLOS Neglected Tropical Diseases, March 2015, p. 1-17) point out to the difficulties of differential diagnostics with infections by a member of the flaviviridae family. In the test described there the NS1 proteins are used for immunological diagnostics.

US 2004/0197769 discloses a diagnostic test for detecting the West Nile virus, the Japanese encephalitis virus, the St. Louis encephalitis virus, and the dengue virus. Thereby, the sample is contacted with antigens applied to a solid phase, namely the "non-structural protein 5" and the "envelope protein". However, more recent developments have shown that the non-structure protein 5 (NS5) is not as specific as assumed. Alves et al., Clinical and Vaccine Immunology, 2016, Vol. 23, No. 6, pp. 460-469 had shown that the dengue virus NS5 protein between the four DENV serotypes has the highest homology and due to highly preserved NS5 epitopes reacts strongly cross-reactive. This is contrary to the statements of US 2004/0197769 according to which NS5 is to be highly specific and suitable to make distinction between various flaviviruses, including the typing of the dengue virus 1-4.

Patentee Susan J. Wong herself in her current publication Wong et al., EBioMedicine (2017), points out that it would be expedient to identify suitable specific epitopes of NS1, NS5, and envelope protein for a virus-specific serological diagnosis and to establish these for diagnostic purposes.

WO 2016/022071 discloses a "point of care test" for detecting dengue viruses. However, no test method for differentiating various closely related flaviviruses is disclosed.

WO 2016/069245 discloses a device for detecting pathogens of various febrile diseases. However, differentiation of various closely related pathogens is neither intended nor disclosed.

Gineer et al., Travel Medicine and Infectious Disease (2016), Vol. 14, pp. 16-20 confirm that the serological differentiation between a dengue virus and a Zika virus infection is difficult due to the high cross-reactivity. Also Carod-Artal, Rev. Neurol., 2016, 62 (7): 317-328 confirms the diagnostic difficulties that occur when an infection with the Zika virus is to be differentiated from other flavivirus infections such as dengue, yellow fever, or West Nile fever as well as from a Chikungunya virus infection.

With regard to the similarity of the symptoms of the viral infections and the possible multiple infections there is therefore considerable interest in reliable differential-diagnostic methods that can be carried out easily and take into account the particular difficulties, especially the problem of cross-reactions.

According to the invention an immunological differential diagnosis to differentiate an infection by dengue virus, Zika virus and Chikungunya virus is preferred. In addition, also the detection of a yellow fever infection or vaccination can be shown as well as the differential-diagnostic differentiation.

The dengue virus is a virus having a single-stranded RNA genome in plus-strand orientation. The dengue virus belongs to the genus flavivirus of the flaviviridae family. Also members of this family are the yellow fever virus, the West Nile virus, the Japanese encephalitis virus, the St. Louis encephalitis virus and the tick-borne encephalitis virus, which can also occur frequently in the foothills of the Alps.

The Zika virus also belongs to the genus flavivirus. In 1947, the Zika virus was discovered in Uganda and only sporadic outbreaks of the virus were observed. However, in recent years there has been an explosive spread of the virus wherein the clinical symptoms can range from almost symptom-free, over a mild febrile disease up to severe cases with neurological complications. Meanwhile it is assumed that the Zika virus may also be transmitted by sexual activities. In infections during pregnancy, cases of microcephalia have often been observed. Therefore, a reliable differential diagnostics is important especially when the female patient is a pregnant woman. It should also be noted that the Zika virus has a particularly high genetic homology to the dengue viruses, which is generally a problem in their differentiation.

Another virus of the arboviruses is the Chikungunya virus that belongs to the family of the Togaviridae, genus alpha virus. Dengue, Zika, and Chikungunya viruses are transmitted to the human being by mosquitos of the genus Aedes and can cause very similar clinical symptoms such as fever, pains in the joints, headache, exhaustion, vertigo, and vomiting.

It is the object of the present invention to provide a method for the immunological diagnosis of a probable infection with one or more arboviruses, wherein it is to be ascertained with which viruses the patient has been infected.

In the first days after onset of the symptoms the pathogen can be detected by means of nucleic acid detection. However, generally this is no longer possible towards the end of the acute phase. Then, according to International guidelines (WHO, CDC) a serological test is the method of choice.

In addition, an immunological diagnosis method has the advantage that the titers of IgM and IgG, respectively can be used to characterize the course of the disease (acute phase, recent and expired/far past infection). Once infected with an arbovirus first the IgM titer sharply increases and then, falls below the detection limit within the next weeks or months, respectively. The IgG titer increases with a slight delay in time and often remains detectable for decades. In the event of renewed contact with the pathogen the IgG titer increases to a significantly higher level, whereas the IgM titer increases considerably less compared to the primary infection and may even be under the detection limit.

The object of the present invention is a method for the immunological diagnostics, in particular the differential diagnostics, of a sample of a patient for a potential infection with an arbovirus.

In the method first the sample of the patient is brought into contact with a plurality of antigens that, spatially separated from each other, were applied to a solid phase. In a preferred embodiment, the sample is a sample containing antibodies, i.e. a serum and/or plasma sample. Other body fluids of a patient, such as for example liquor or mother's milk, can also be employed in the method.

With the antigens several different proteins or peptide fragments having at least 8, preferably 12 and particularly preferred 40 amino acids are employed. In the methods or kits for performing said methods according to the invention the antigens listed in detail below are employed. It is possible to employ the complete proteins or also fragments of these proteins with the immunologically reactive parts. Since the sequences of the antigens are known the proteins or protein fragments can recombinantly be prepared in a known manner. In order to find out which parts are immunologically reactive usually those parts are expressed that in the antigens are located in places that are presented to the immune system. Which parts are particularly suitable can be easily determined by recombinantly preparing the exposed fragments and testing with known patient sera. These known well defined patient sera originate from such patients in whom the infection with a certain virus has been surely detected via the various diagnosis options.

When using fragments these have at least 8, in general at least 40, preferably at least 60 and particularly preferred at least 80 amino acids. Also particularly preferred are such antigens that correspond to the full-length protein or contain at least 80%, preferably at least 90% and particularly preferred at least 95% of the full-length antigen. According to the invention it is preferred to employ proteins that are to 80% and particularly preferred to 90%, and particularly preferred to 95% identical to the full-length proteins of the NS1 and E proteins. A particularly high identity is preferred with the E proteins in the domains I-III. In a preferred embodiment, fragments of at least 10, preferably at least 20 amino acids are not expressed at the N-terminus or at the C-terminus or at both ends.

Preferably, these are the following antigens:

a) "non-structural protein 1" (NS1 antigen) of the dengue virus

There are four serotypes of the dengue virus named DENV-1, DENV-2, DENV-3, and DENV-4. According to the invention, preferably the NS1 of serotype 2 (DENV-2) is employed. NS1 is a highly preserved glycoprotein that seems to be essential for the survivability of the virus, but still no definite biological activity was assigned to this antigen. Actually unusual for a viral glycoprotein the NS1 is produced both in a membrane-associated and in a secreted form. Therefore, the NS1 antigen is present in high concentrations in the serum of patients infected with the dengue virus during the early clinical phase of the disease. The complete genome sequences of the dengue virus types 1-4 were published by Añez et al., Genome Announcements (2016), Vol. 4, No. 1, p. 1-2.

b) "envelope protein" of the dengue virus

A further protein employed in the test method according to the invention is the "envelope protein" of the dengue virus serotype 2. The envelope protein E is the main antigen for the humoral immune response. Mutations occurring therein can affect the virulence of the dengue virus.

c) "envelope protein 1" of the Chikungunya virus

A further antigen employed in the test is the "envelope protein 1" of the Chikungunya virus or an immunologically reactive part thereof having at least 40 amino acids. In the meantime, three phylogenetically distinguishable groups of the Chikungunya virus are known, namely the Asian genotype, the West African genotype, and the East, Central and South African genotype. The genome of the Chikungunya virus is a plus-stranded RNA genome of about 12,000 nucleotides. It contains two open reading frames, wherein the second reading frame codes for the structure proteins C, E1, E2, and E3. A complete genome sequence of the Chikungunya virus named GD05/2010 is available in the gene library under the access number JX088705 (Li et al., Journal of Virology (2012), Vol. 86, No. 16, p. 8904-8905).

By employing this E1 protein it can be ascertained whether or not there is an infection with a Chikungunya virus. Alternatively, also "virus-like particles" (VLP) of Chikungunya can be employed. Such VLPs may be prepared for example in insect cells and also used for vaccinations ([DeZure et al., JID 2016: 214 (Suppl. 5)]).

d) NS1 protein of the Zika virus

A further antigen employed in the test is the "non-structural protein 1" (NS1) of the Zika virus or an immunologically reactive part thereof having at least 40 amino acids. The genome of the Zika virus consists of an RNA of ca. 10,000 nucleotides in length that codes a polyprotein that has all structural proteins. The genome organization comprises the proteins C, prM, E, NS1, NS2a, NS2b, NS3, NS4a, NS4b, and NS5.

e) "envelope protein" of the Zika virus

The "envelope protein" is abbreviated with "E". A complete nucleotide sequence of a Zika virus was deposited in the gene library under the access number KU321639 (Cunha et al., Genome Announcements, March/April 2016, Volume 4, Issue 2, pp. 1-2).

That is, in the method according to the invention both the non-structural protein 1 and the envelope protein of a Zika virus are employed.

In a further embodiment as the antigen it is also employed:

f) NS1 protein of the yellow fever virus (YFV)

The genome of the yellow fever virus codes for the three structural proteins C, prM, E and in the seven non-structural proteins NS1, NS2A, NS2B, NS3, NS4A, NS4B, NS5. The same applies to DENV and ZIKV. According to the invention, a peptide from the NS1 protein or a protein fragment thereof is used. For journeys to yellow fever endemic areas, vaccination with an attenuated virus strain is mandatory. It can therefore be of advantage to also use the NS1 protein of the yellow fever virus in the method.

According to the invention, some preferred constructs of fragments or immunologically highly relevant peptide fragments have been produced that are particularly preferred in the test method and the test kits. These are the following constructs (sub-fragments) of the envelope protein of the dengue and Zika virus, respectively. The constructs tested in addition to the envelope protein sequences still have a C-terminal His-tag and a protease cleavage site (the antigen sequences of DENV and ZIKV are underlined):

Domain III of the envelope protein of dengue virus serotype 2 (strain 16681) with protease cleavage site and His-tag:

(SEQ ID NO: 1)
MYSMCTGKFKVVKEIAETQHGTIVIRVQYEGDGSPCKIPFEIMDLEKRHV

LGRLITVNPIVTEKDSPVNIEAEPPFGDSYIIIGVEPGQLKLNWFKKGLE

VLFQGPHHHHHHHH.

Domain III of the envelope protein of the Zika virus (strain SPH2015) with protease cleavage site and His-tag:

(SEQ ID NO: 2)
MYSLCTAAFTFTKIPAETLHGTVTVEVQYAGTDGPCKVPAQMAVDMQTLT

PVGRLITANPVITESTENSKMMLELDPPFGDSYIVIGVGEKKITHHWHRS

GLEVLFQGPHHHHHHHH.

These fragments could preferably be used in the tests.

Preferably employed sub-fragments are the following NS1 peptides that can be used for differentiation:

Peptides of the NS1 protein. In the following, here only the sequences for dengue virus serotype 2 strain 16681; NS1 are listed; corresponding sequences can easily be found in the sequences of other serotypes and viruses of the flaviviridae family:

(SEQ ID NO: 3)
KRSLRPQPTELKYSWKTWGKAKMLSTESHNQT (SEQ ID NO: 4)
PWHLGKLEMDFDFCD (SEQ ID NO: 5)
DSGCVVSWKNKELKCGSGIFITDN.

The above-mentioned fragments with SEQ ID NOs 3, 4, and 5 that are preferably used have been chosen because these are fragments of the antigens against which the immune system of the infected patients preferably produces antibodies. However, these antibodies are easily distinguishable from each other, namely in that, if there are present antibodies against the given fragments of the NS1 protein of the dengue virus, these do not react with the homologous regions of the NS1 protein that comes from the Zika virus. The same applies conversely. Background of this finding could be that due to the high homology between the dengue and the Zika virus a differentiation on the basis of linear epitopes is not possible or only hardly possible. Since also the three-dimensional structure of both NS1 antigens might be very similar, it is assumed according to the invention that the main difference between the chosen fragments of the NS1 of dengue virus and Zika virus is in charge differences at the surfaces of both proteins.

The above-mentioned fragments that are preferably used make use of this difference for differentiation. By comparing the sequences of dengue and Zika NS1 and the use of a three-dimensional model further such sequences can be found. When using antigen fragments these peculiarities have to be taken into account and there must be chosen areas for the peptides that are responsible for different antigenic areas. This can lead to the preferential use of full-length proteins or proteins at least 90% of which correspond to full-length proteins, unless immunologically distinguishable regions can be identified.

In a preferred embodiment, full-length proteins are employed, wherein differentiation is made via the direct reactivity comparison of homologous proteins, i.e. dengue-NS1 vs. Zika-NS1. When using fragments with the E protein these are preferably the domains I to III. DENV-2 are amino acids 1-395 of totally 495, with the ZIKV-E protein AA 1-404 of totally 505 AA. For objectivization of the reactivity comparison preferably mechanical means are used, i.e. scans and a suitable evaluation software.

The antigens are applied to a solid phase. There are several ways in which this can be done. In a preferred embodiment, the antigens are applied to a carrier strip as bands. In this case, one speaks of a so-called line assay. Alternatively, the antigens, spatially separated from each other, can be applied to ELISA test plates, wherein one antigen and several spatially separated antigens, respectively can be inserted into one reaction vessel (protein chip/array) and coupled to the solid phase. A further embodiment is that the antigens are preferably coupled to magnetizable beads. In this way, the antigens can conveniently be contacted with the sample and removed from the reaction mixture again.

After the antigens coupled to the solid phase and the sample have reacted an immune complex of the antigen and the antibodies specifically binding thereto is formed. In order to avoid non-specific bindings on the one hand in the production of the test kits all the locations are saturated that could cause a non-specific binding. Such non-specific binding sites can be parts of the carrier. However, after the reaction antibodies that were not specifically bound have to be separated. In a preferred embodiment this is done by washing with suitable washing solutions or buffers.

On the solid phase, by the reaction of the antigen with specific antibodies directed against it an immune complex has formed that has to be converted into an evaluable signal, provided that specific antibodies are present in the sample. There are many different ways for the conversion of the immune complex formed on the solid phase into an evaluable signal. Preferably, such a conversion has to be (semi) quantitative, because it is required for the evaluation of the test results that the relative strengths of the signals can be compared.

In a preferred embodiment, the immune complex on the solid phase is made visible in that an anti-antibody is added that is coupled to a signaling agent. The anti-antibody usually are polyclonal antibodies generated in laboratory animals (for example, rabbits, goats) that are directed against human IgG antibodies or human IgM antibodies. The anti-antibodies usually are directed against the Fc part of the antibodies from the patient sample that have bound to the respective antigens.

The anti-antibodies are coupled to a signal-generating agent. This can be an agent that directly generates a signal, i.e. for example a dye or a fluorescent dye. However, it can be an agent that amplifies the signal. In a preferred embodiment, this is an enzyme, such as for example horse-radish peroxidase or alkaline phosphatase. The enzyme converts a substrate into a measurable signal, for example a dyed product. The longer the enzyme can act on the substrate the stronger is the dyed signal.

The reaction is terminated after a pre-determined time in that washing is performed, for example.

In the method according to the invention a so-called "cut-off" is used to consider the noise that can always occur in immunological tests. Said cut-off for example is on the test strip and thereby is tested under the same conditions as the samples to be examined. The cut-off of the test or the intensity of the cut-off band, respectively are adjusted such that defined negative sample groups are below the cut-off and defined positive groups are above the cut-off.

After having carried out the test and having converted the immune complex into a measurable signal the intensity of the signal is evaluated. This is based on the assessment set out in table 1:

TABLE 1

Scheme of Evaluation

| Intensity of the Signal | Evaluation |
| --- | --- |
| no reaction | − |
| reactivity below the cut-off band | +/− |
| reactivity equal to the cut-off band | + |
| reactivity stronger than the cut-off band | ++ |
| reactivity significantly stronger than the cut-off band | +++ |
| maximum reactivity | ++++ |

The evaluation set out in table 1 is the visual evaluation. Of course, the measurement can be carried out also with suitable instruments, for example accordingly adjusted photometers. Then, the intensity of the signal can be assigned to a certain, objectively measureable value.

In a preferred embodiment, the test method is carried out with the same sample for the IgG and IgM detection and both presence and absence of IgM and IgG antibodies against the antigens is determined. A test kit suitable for that contains all the reagents needed for that.

The test can also be machine-evaluated which leads to more objective results. Thereby, response intensity is measured with a suitable device (scanner etc.) and the measured values obtained are calculated with a suitable program.

In a preferred embodiment, in the method according to the invention the test strips are evaluated computer-assisted by means of test strip evaluation software. Here, the developed test strips are read in by a scanning method and the signal strengths characterized by the intensity of color (gray levels) of the individual antigen bands are measured. On the one hand, this enables the direct comparison of the signal strengths of two or more antigen bands and on the other hand the comparison of the individual band intensities with the cut-off intensity. In contrast to the visual evaluation the exact ratio of band intensities to each other or to the cut-off intensity (cut-off index value) can be shown.

Preferably, the method according to the invention can be carried out with accordingly adapted test kits. These test kits contain the above-mentioned test strips with the corresponding antigens, control bands (i.e. cut-off band) and the reagents for washing the test strips or test microwell plates. Moreover, the test kits often contain positive and negative control sera and reaction controls.

Due to the difficulties inherent to the differential diagnosis (high similarity of the antigens, multiple infections) as much information as possible should be used for the evaluation. This involves anamnesis of the patient, if available. Moreover, depending on the design of the specific situation, it may be advantageous if both the IgM response and the IgG response are performed against the same antigens. For example, this can give an indication for fresh infections or far past infections. Also multiple infections can be detected.

In a particularly preferred embodiment the test is performed as a line immune assay. This test principle involves separately lining-up the single antigens on special locations onto the test strips, which enables identification of specific antibodies against the single antigens of dengue, Chikungunya and Zika viruses. In a particularly preferred embodiment such a line immune assay contains the recombinantly produced full-length antigens NS1 and the E protein of the dengue virus, at least one Chikungunya virus antigen such as for example the E1 protein and the NS1 and the E protein of the Zika virus. The E1 protein of the Chikungunya virus optionally can also be replaced by virus-like particles of the Chikungunya virus. The test according to the invention results in reactions of different strengths with the antigens preferably employed. In difficult cases, the serologic evaluation can be made in connection with the results of the IgG and IgM test, wherein the time of the infection or the time of sampling after onset of clinical symptoms and optionally the travel history of the last six weeks can be taken into account.

In case of primary flavivirus infections usually insignificant cross-reactivities between the genetically related flaviviruses are observed.

On the other hand, in case of secondary flavivirus infections increasingly heterologous, i.e. antibodies cross-reacting with other flaviviruses can be formed. Cross-reacting antibodies appear in greater strength between the dengue and Zika virus. But also sera of patients with a previous infection or with vaccination against other flaviviruses (such as yellow fever virus, West Nile virus, tick-borne encephalitis virus, St. Louis encephalitis virus, or Japanese encephalitis virus) can cause cross-reactions in serological tests.

In general, IgM immune response against flaviviruses is more specific compared to the IgG immune response. This especially applies to a flavivirus secondary infection, i.e. when the patient already had one or more flavivirus infection(s). However, since the IgM response in a secondary infection generally is significantly lower or not detectable at all it is of advantage if an indication to the pathogen can be obtained by means of an IgG immune response. The direct comparison of the antibody responses against e.g. NS1 in the IgG test often results in indications to the infection pathogen. However, here it must be noted that in case of acute infections generally there has not yet been the IgG response against the current pathogen. That is, with samples from the acute phase here a subsequent sample at intervals preferably of 1-2 weeks is necessary. This is shown in example 1, patient 4.

Differentiation between dengue and Zika virus is preferably possible on the basis of the specific NS1 antigen reactivities. A multiple infection with the dengue virus should not result in an equally strong reactivity of the dengue and Zika NS1 antigens.

If equally reactive bands of dengue and Zika virus E proteins are present with simultaneously lacking reactivity with NS1 of the dengue and Zika viruses no reliable flavivirus differentiation can be made. If the sample was taken only a few days after onset of the symptoms it may be useful to test a subsequent sample. Especially, a weak IgG reactivity with both (DENV and ZIKV) E proteins present at this early stage may be attributable to a previous infection with another flavivirus or a flavivirus vaccination. Formation of specific anti-dengue or anti-Zika virus antibodies, especially against the NS1 antigen, can still take place.

If at least one antigenic band selected from dengue virus NS1, dengue virus E protein, Zika virus NS1, and Zika virus E protein reacts clearly positive there is an immune response against a flavivirus infection. If no band reacts or only bands of very weak intensities below the cut-off are found the result for dengue and Zika viruses is negative.

The following Table A applies to the differentiation between dengue virus and Zika virus by means of NS1:

| Sampling after onset of clinical symptoms | IgG and/or IgM NS-1 antigen pattern | Interpretation |
|---|---|---|
| ≥ more/less 4-6 days | DENV NS-1 band reacts with the same (+) or enhanced intensity as the cut-off band and is clearly visible more colored than the ZIKV NS-1 band | flavivirus positive, suspicion of dengue |
| ≥ more/equal 4-6 days | DENV NS-1 and ZIKV NS-1 bands react with the same (+) or enhanced intensity as the cut-off band and are equally colored without a clearly visible difference. | flavivirus positive, no differentiation, positive NS-1 is specific for DENV and ZIKV |
| ≥ more/equal 4-6 days | ZIKV NS-1 band reacts with the same (+) or enhanced intensity as the cut-off band and is clearly visible more colored than the DENV NS-1 band. | flavivirus positive, suspicion of Zika |

The following Table B applies to the detection of the Chikungunya virus:

| | |
|---|---|
| CHIKV E1 antigen band reacts with the same (+) or enhanced intensity as the cut-off band | Chikungunya positive |
| no CHIKV E1 antigen band (−) or CHKV E1 antigen band of weaker (±) intensity than the cut-off band | Chikungunya negative |

It should be emphasized that the test method according to the invention gives clear, measureable reaction differences that are to be interpreted in the overall context due to the complexity of the problem.

The invention is further explained in the examples:

EXAMPLE 1

A so-called "line assay" test strip with the antigens employed according to the invention was prepared, wherein the individual antigens were applied at different points of the test strip. These test strips were reacted with sera of four different patients. The results are illustrated in FIG. 1. This was about:

Patient 1: The patient did not show any IgG antibody reactions against dengue, Chikungunya, and Zika viruses, but IgM antibodies against the ZIKV NS1 protein. Thus, the patient has fresh or recent Zika virus infection. The infection is relatively simple to prove, since it is a singular flavivirus first infection.

Patient 2: The patient has IgG antibodies both against dengue and against Zika viruses. The direct comparison of the corresponding antibodies against DENV/ZIKV NS1 shows that the antibody titer of the dengue virus NS1 is significantly stronger (++++) than the corresponding one of the Zika virus NS1 (++). The same applies to the corresponding E proteins of the dengue (+++) and Zika viruses (++). In a direct comparison of the IgG antibody titer it is therefore possible to distinguish between anti-dengue and anti-Zika virus IgG antibodies. Moreover, the patient has IgM antibodies that are exclusively directed against the dengue virus antigens. Based on the IgM response (dengue virus NS1 (++), dengue virus E (++)) it can be stated that the patient had an acute or recent DENV infection.

Patient 3: The patient has both IgG antibodies against dengue virus and antibodies against the Zika virus. A direct comparison of the corresponding antibodies against DENV/

ZIKV NS1 shows that the antibody titer of the dengue virus NS1 is significantly higher (stronger) (++) than the corresponding one of the Zika virus NS1 (+/−). Based on the corresponding E proteins of the dengue virus (+) and the Zika virus (+) it cannot be differentiated. Here, too, it is possible to make a statement by comparing the anti-NS1 IgG antibody titers. Further, the patient has IgM antibodies against the NS1 protein of the dengue virus (++). The patient has an acute or recent DENV infection.

Patient 4: The patient has no IgG antibodies against the dengue virus NS1 (−), but antibodies against the Zika virus NS1 (++). The antibodies against DENV E (++) and ZIKV E do not allow differentiation. Here, by the antibodies directed against NS1 it is possible to deduce a Zika virus infection. However, the IgM test strip, not illustrated here, is negative. This leads to assume that it is a past infection.

Altogether, the evaluation of the test was illustrated in table 2 below:

Evaluation: the different intensities of the bands are shown with −, +/−, +, ++, +++, ++++. RK is a reaction control that has to be present. IgG or IgM indicates the respective class of immunoglobulins. The bands are always evaluated in comparison to the cut-off band. DENV NS1, DENV E (A), DENV E (B), CHIKV E1, ZIKV NS1, ZIKV E (A), and ZIKV E (B). Variants (A) and (B) each correspond to two different antigen concentrations.

Figure 3:
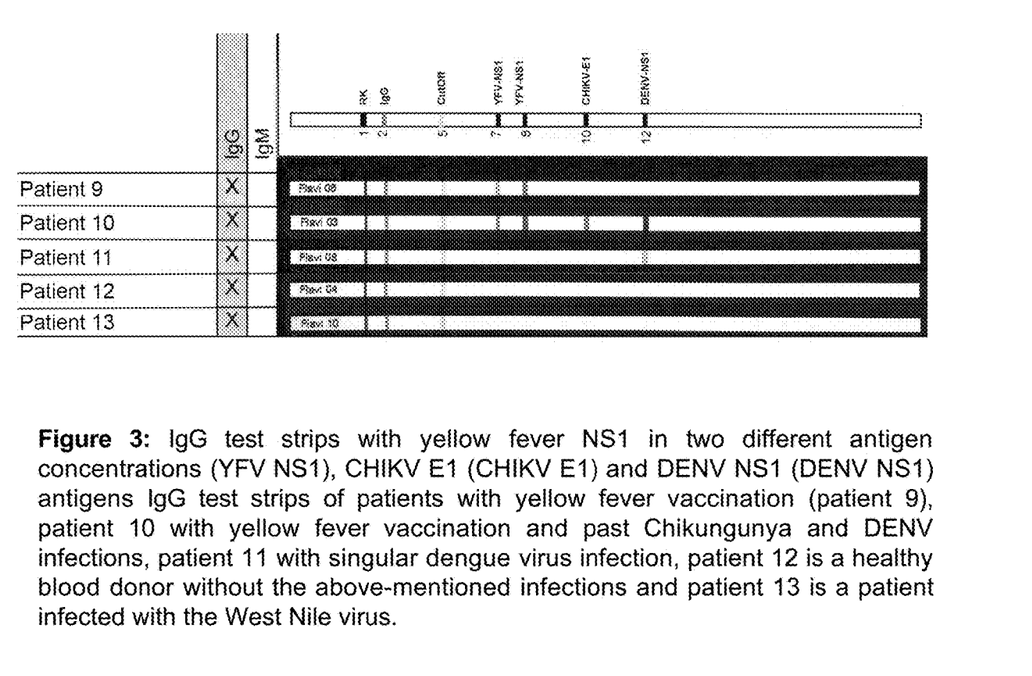
FIG. 3 shows IgG test strips with yellow fever NS1 in two different antigen concentrations (YFV NS1), CHIKV E1 (CHIKV E1) and DENV NS1 (DENV NS1) antigens IgG test strips of patients with yellow fever vaccination (patient 9), patient 10 with yellow fever vaccination and past Chikungunya and DENV infections, patient 11 with singular dengue virus infection, patient 12 is a healthy blood donor without the above-mentioned infections and patient 13 is a patient infected with the West Nile virus.

Patient 9 was vaccinated within the last two years against yellow fever and accordingly shows a response to the yellow fever virus NS1 antigen in the IgG detection, there is not any cross-reactivity with the other pathogens. Patient 10 is vaccinated against yellow fever and further has IgG antibodies against the Chikungunya and dengue viruses. NS1 antigens of the yellow fever and dengue viruses as well as the E1 antigen of the Chikungunya virus react. Patient 11 is an example for a past singular dengue virus infection (patient with dengue fever 7 years ago) and it is seen that there is not any cross-reactivity to yellow fever (flavivirus) and Chikungunya virus. Patient 12 is a healthy blood donor from Germany without the above-mentioned infections who acts as a negative control. Patient 13 is a patient infected with West Nile virus, s/he has not any cross-reactivity to the other pathogens.

EXAMPLE 4

Two test strips were prepared that contained the dengue virus (serotype 2) envelope protein (DENV E) and a subfragment of the envelope protein consisting of the domain III (DENV EDIII). The test strips were reacted with the sera of patients 14 and 15, wherein both patients are serologically positive for IgG antibodies against dengue and Chikungunya

TABLE 2

Summary of the Evaluation of Patients 1-4.

| Patient | IgG/M | DENV NS1/ D2 NS1 | DENV E (A)/ D2 E | DENV E (B)/ n.a. | CHIKV E1/ CHIKV E1 | ZIKV NS1/ ZIKV NS1 | ZIKV E (A)/ ZIKV E | ZIKV E (B)/ n.a. |
|---|---|---|---|---|---|---|---|---|
| 1 | IgG | − | − | − | − | − | − | − |
| 1 | IgM | − | − | n.a. | − | ++ | − | n.a. |
| 2 | IgG | ++++ | +++ | +++ | − | ++ | ++ | ++ |
| 2 | IgM | ++ | ++ | n.a. | − | − | − | n.a. |
| 3 | IgG | ++ | + | + | − | +/− | + | + |
| 3 | IgM | ++ | − | n.a. | − | − | − | n.a. |
| 4 | IgG | − | ++ | ++ | − | ++ | ++ | ++ |
| 4 | IgM | | | | n.a. | | | | n.a. is the abbreviation for "not available" and indicates that the IgM test strip does not contain the corresponding antigen band.

EXAMPLE 2

Further, a line assay with sera of patients in whom a differentiation between the dengue virus and Zika virus is possible by comparing the intensity of the bands was carried out. The results are illustrated in FIG. 2.

FIG. 2 contains exemplary strips with samples of patients 5-8 in whom a differentiation between DENV and ZIKV in the IgG test is possible by directly comparing the DENV and ZIKV NS1 band intensities. The IgM test results are negative which gives an indication of past infections.

Both DENV and ZIKV NS1 are positive (react more strongly compared to the cut-off band). However, by the direct comparison of the intensities of both antigens it is seen that the respective DENV NS1 band is clearly more colored on the test strips compared to the ZIKV NS1 band.

Patients 5-8 have a past DENV infection and no ZIKV infection, patient 6 additionally has a past CHIKV infection.

EXAMPLE 3

FIG. 3 contains exemplary strips with samples of patients 9-13 in whom a differentiation between yellow fever, Chikungunya, dengue, and West Nile viruses is possible.

viruses. The example illustrates that the test cannot only be carried out with the full-length antigens, but also with suitable fragments.

EXAMPLE 5

According to example 2 line assay test strips for the detection of antibodies against the dengue virus NS1 and E protein, the Chikungunya virus E1 protein, and Zika virus NS1 and E protein were prepared and tested with patient samples.

The first patient group (a) comprises patients who have returned to Germany after staying in an endemic area for one or more of the three mentioned pathogens. The second patient group (b) comprises patients from a dengue virus endemic area in Latin America who have IgG antibodies against the dengue virus.

The evaluation of the results was with the automatic test strip evaluation software recomScan. In analogy to example 2 the serological differentiation between a dengue and a Zika virus infection could be made by directly comparing the DENV-NS1 and ZIKV NS1 band intensities.

TABLE 3

Tables 3a and 3b, on the one hand contain the intensity of DENV-NS1 and ZIKV-NS1 bands and the cut-off index values (COI; value of the signal related to the cut-off) of the individual antigen bands. According to the visual evaluation a COI value ≥1 is judged to be a positive signal. The differentiation between DENV and ZIKV is only made if DENV NS1 and/or ZIKV NS1 have a COI value ≥1 and one of the both NS1 bands has at least twice the intensity of the other NS1 band.

(a) Patient group of returnees (recent infections):
- Patients 16 and 19: dengue virus positive preliminary finding (nucleic acid detection)
- Patients 17 and 18: Zika virus positive preliminary finding (nucleic acid detection) One sample each was tested from patients 18 and 19 following the convalescence phase after a recent infection and a subsequent sample after several months. The results of the first sampling each are given in table 3a in the upper line, that of the subsequent sample in the line below.

Patient 16 has had a dengue virus infection in the past. Typically, the IgM titer is significantly lower compared to the primary infection as a result of a secondary infection and the IgG response has a higher flavivirus cross-reactivity. Nevertheless, in the IgG test it is possible to serologically differentiate between an antibody response against the dengue and Zika viruses by a direct NS1 comparison of both pathogens. In the example mentioned an IgG immune response against dengue, but not against the Zika virus is detected on this basis. Thus, based on the IgG test results a recent Zika virus infection can be excluded. Patients 17 and 18 (first sampling) are IgG and IgM seropositive for ZIKV. Several months after the infection the subsequent sample of patient 18 as expected has only anti-ZIKV IgG antibodies. The first sampling from patient 18 is IgG and IgM, the second only IgG positive for ZIKV. Patient 19 (first sampling) is IgG and IgM seropositive for DENV. Several months after the infection the subsequent sample of patient 19 as expected has only Anti-DENV IgG antibodies.

TABLE 3a (a)

| | IgG Antibody Detection | | | | | | | | | |
|---|---|---|---|---|---|---|---|---|---|---|
| | Intensity | | COI (Cut-off Index Values) | | | | | Test Interpretation: | | |
| | DENV | ZIKV | DENV | | CHIKV | ZIKV | | IgG positive for | | |
| | NS1 | NS1 | NS1 | E | E1 | NS1 | E | DENV | ZIKV | CHIKV |
| Patient 16 | 257 | 89 | 5.5 | 3.7 | 0 | 1.9 | 1.7 | x | | |
| Patient 17 | 0 | 243 | 0 | 3.4 | 0 | 4.7 | 1.6 | | x | |
| Patient 18 | 0 | 166 | 0 | 0 | 0 | 3.2 | 0 | | x | |
| | 0 | 345 | 0 | 0.3 | 0 | 6.9 | 0.4 | | x | |
| Patient 19 | 68 | 0 | 1.3 | 0 | 0 | 0 | 0 | x | | |
| | 242 | 14 | 4.7 | 3.9 | 0 | 0.3 | 0.4 | x | | |

| | IgM Antibody Detection | | | | | | | | | |
|---|---|---|---|---|---|---|---|---|---|---|
| | Intensity | | COI (Cut off Index Values) | | | | | Test Interpretation | | |
| | DENV | ZIKV | DENV | | CHIKV | ZIKV | | IgM positive for | | |
| | NS1 | NS1 | NS1 | E | E1 | NS1 | E | DENV | ZIKV | CHIKV |
| Patient 16 | 10 | 0 | 0.3 | 0.4 | 0 | 0 | 0 | | | |
| Patient 17 | 13 | 118 | 0.3 | 0 | 0 | 2.9 | 2 | | x | |
| Patient 18 | 24 | 240 | 0.5 | 0.8 | 0 | 5.1 | 0.2 | | x | |
| | 0 | 0 | 0 | 0 | 0 | 0 | 0 | | | |
| Patient 19 | 262 | 0 | 6.8 | 1.7 | 0 | 0 | 0.2 | x | | |
| | 0 | 0 | 0 | 0 | 0 | 0 | 0 | | | |

(b) Examples of samples from Dengue virus endemic areas. Samples were selected that had a DENV IgG titer. 13/23 samples show both a DENV NS1 and a ZIKV NS1 signal above the cut-off. However, by the direct NS1 comparison a differentiation is possible.

TABLE 3b (b)

| | IgG Antibody Detection | | | | | | | | | |
|---|---|---|---|---|---|---|---|---|---|---|
| | Intensity | | COI (Cut-off Index Values) | | | | | Test Interpretation: | | |
| | DENV | ZIKV | DENV | | CHIKV | ZIKV | | IgG positive for | | |
| | NS1 | NS1 | NS1 | E | E1 | NS1 | E | DENV | ZIKV | CHIKV |
| Patient 20 | 404 | 119 | 9.7 | 8.9 | 0 | 2.9 | 6 | x | | |
| Patient 21 | 116 | 0 | 2.5 | 4.8 | 0 | 0 | 3.2 | x | | |

TABLE 3b-continued (b)

| | IgG Antibody Detection | | | | | | | | |
|---|---|---|---|---|---|---|---|---|---|
| | Intensity | | COI (Cut-off Index Values) | | | | | Test Interpretation: IgG positive for | |
| | DENV | ZIKV | DENV | | CHIKV | ZIKV | | | | |
| | NS1 | NS1 | NS1 | E | E1 | NS1 | E | DENV | ZIKV | CHIKV |
| Patient 22 | 47 | 0 | 1.1 | 6.3 | 8.4 | 0 | 4.4 | x | | x |
| Patient 23 | 322 | 0 | 7.4 | 6.5 | 0 | 0 | 2.7 | x | | |
| Patient 24 | 359 | 132 | 8.3 | 7.2 | 0 | 3 | 5.4 | x | | |
| Patient 25 | 321 | 9 | 8 | 8.3 | 11.1 | 2.5 | 5.9 | x | | x |
| Patient 26 | 463 | 67 | 10.7 | 10.6 | 0 | 1.5 | 6.4 | x | | |
| Patient 27 | 347 | 38 | 7.6 | 6.8 | 0 | 0.8 | 4.4 | x | | |
| Patient 28 | 407 | 117 | 8.7 | 7.9 | 0 | 2.5 | 5.5 | x | | |
| Patient 29 | 305 | 99 | 6.6 | 6.5 | 9.3 | 2.2 | 5 | x | | x |
| Patient 30 | 256 | 28 | 5.4 | 7.4 | 0 | 0.6 | 5 | x | | |
| Patient 31 | 456 | 197 | 9.6 | 9.2 | 0 | 4.1 | 6.3 | x | | |
| Patient 32 | 497 | 179 | 10.1 | 9.3 | 0 | 3.6 | 6.3 | x | | |
| Patient 33 | 330 | 103 | 6.2 | 3.9 | 0 | 1.9 | 2.6 | x | | |
| Patient 34 | 284 | 122 | 6.2 | 8.3 | 0 | 2.7 | 5.5 | x | | |
| Patient 35 | 265 | 35 | 5.7 | 5.8 | 7.9 | 0.7 | 4.6 | x | | x |
| Patient 36 | 371 | 146 | 7.2 | 6.4 | 0 | 2.8 | 4.6 | x | | |
| Patient 37 | 324 | 59 | 7.6 | 2.2 | 0 | 1.4 | 1.3 | x | | |
| Patient 38 | 359 | 35 | 9.2 | 7.5 | 0 | 0.9 | 5.4 | x | | |
| Patient 39 | 472 | 180 | 10.9 | 10.9 | 0 | 4.2 | 5.7 | x | | |
| Patient 40 | 368 | 11 | 7.9 | 6.3 | 0 | 0.2 | 4 | x | | |
| Patient 41 | 217 | 15 | 4.6 | 7.4 | 0 | 0.3 | 5.8 | x | | |
| Patient 42 | 235 | 36 | 4.6 | 2.7 | 0 | 0.7 | 1.8 | x | | |

FIG. 5 shows the results of a test: IgG and IgM test strips with DENV NS1, DENV E, CHIKV E1, ZIKV NS1, and ZIKV E antigens were employed. Patient 43 had past ZIKV and CHIKV infections. Patient 44 had an acute/recent dengue virus infection (IgG and IgM positive for DENV). Patient 45 is IgG positive for DENV, ZIKV, and CHIKV. However, the acute/recent is an infection with the Zika virus, since for this pathogen there can still be detected anti-ZIKV NS1 IgM antibodies.

The invention claimed is:

1. A method for the immunological differential diagnosis of a sample from a human patient with a potential infection with an arbovirus, wherein
- a) a sample is brought into contact with a plurality of antigens that, separated from each other, are applied to a solid phase, wherein at least the following antigens are used:
  - aa) the non-structural protein 1 of a Dengue virus serotype 2 or an immunologically reactive part thereof having at least 40 amino acids,
  - bb) an envelope protein of a Dengue virus serotype 2 or an immunologically reactive part thereof having at least 40 amino acids,
  - cc) an envelope protein of a Chikungunya virus or an immunologically reactive part thereof having at least 40 amino acids, dd) the non-structural protein 1 of a Zika virus or an immunologically reactive part thereof having at least 40 amino acids and
ee) an envelope protein of a Zika virus or an immunologically reactive part thereof having at least 40 amino acids, b) the solid phase of a) is washed to separate non-specific bindings, c) anti-human IgG and/or anti-human IgM antibodies coupled to a signal-generating agent are added to the washed solid phase of b) and any immune complex formed is detected by a signal from the signal-generating agent, and d) any signal generated in step c) is compared to a negative and positive control, and the presence and/or absence of IgG and/or IgM antibodies against the same antigens is determined by comparing any signal generated in c) with the negative and positive control.

2. The method according to claim 1, characterized in that in the diagnosis method in step a) further includes:
ff) as further antigen a peptide having at least 8 amino acids from the NS1 region of a yellow fever virus.

3. The method according to claim 1, characterized in that the signal generating agent is an enzyme that converts a substrate into a colored product that is visible and/or can be quantitatively measured with a suitable device.

4. The method according to claim 1, characterized in that it is determined for each sample whether the antibodies belong to the class of IgM, IgG or both.

5. A test kit for carrying out a method according to claim 1, characterized in that the test kit contains a plurality of spatially separated solid phases, wherein the test kit has at least the following antigens:
aa) the non-structural protein 1 of a Dengue virus serotype 2 or an immunologically reactive part thereof having at least 40 amino acids,
bb) an envelope protein of a Dengue virus serotype 2 or an immunologically reactive part thereof having at least 40 amino acids,
cc) an envelope protein of a Chikungunya virus or an immunologically reactive part thereof having at least 40 amino acids,
dd) the non-structural protein 1 of a Zika virus or an immunologically reactive part thereof having at least 40 amino acids and
ee) an envelope protein of a Zika virus or an immunologically reactive part thereof having at least 40 amino acids, anti-human IgG and or anti-human IgM antibodies coupled to a signal-generating agent reagents for washing non-specific binding;
reagents for converting any immune complex into an optically visible signal;
and negative and positive controls for comparing signals generated from any immune complex formed through using the kit.

6. The test kit according to claim 5, characterized in that the test kit further includes:
ff) as further antigen a peptide having at least 8 amino acids from a non-structural protein 1 of a yellow fever virus.

7. The method according to claim 1, characterized in that the immunologically reactive part of the employed proteins comprises at least 80% of the full length of each of the proteins.

8. The method according to claim 1, characterized in that the reactive part of the employed proteins comprises at least 95% of the full length of the naturally occurring proteins.

9. The test kit according to claim 5, characterized in that the immunologically reactive part of the employed proteins comprises at least 80% of the full length of the naturally occurring proteins.

10. The test kit according to claim 5, characterized in that the reactive part of the employed proteins comprises at least 95% of the full length of the naturally occurring proteins.

* * * * *